United States Patent
Chang

(10) Patent No.: US 10,983,001 B2
(45) Date of Patent: Apr. 20, 2021

(54) RAMAN PROBE AND BIOLOGICAL COMPONENT ANALYZING APPARATUS USING THE SAME

(71) Applicant: SAMSUNG ELECTRONICS CO., LTD., Suwon-si (KR)

(72) Inventor: Ho Jun Chang, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

(21) Appl. No.: 16/526,456

(22) Filed: Jul. 30, 2019

(65) Prior Publication Data
US 2020/0041338 A1 Feb. 6, 2020

(30) Foreign Application Priority Data
Jul. 31, 2018 (KR) .................. 10-2018-0089268

(51) Int. Cl.
| | |
|---|---|
| *G01J 3/02* | (2006.01) |
| *G01J 3/44* | (2006.01) |
| *A61B 5/1455* | (2006.01) |
| *A61B 5/00* | (2006.01) |

(52) U.S. Cl.
CPC .......... *G01J 3/0216* (2013.01); *A61B 5/0075* (2013.01); *A61B 5/1455* (2013.01); *G01J 3/0218* (2013.01); *G01J 3/4412* (2013.01)

(58) Field of Classification Search
CPC .................................................. G01J 3/0216
USPC ....................................................... 356/301
See application file for complete search history.

(56) References Cited

U.S. PATENT DOCUMENTS

| | | | |
|---|---|---|---|
| 5,615,673 A | 4/1997 | Berger et al. | |
| 6,115,528 A * | 9/2000 | Schmucker | G01N 21/01 356/301 |
| 6,333,784 B1 | 12/2001 | Blasi et al. | |
| 6,370,406 B1 * | 4/2002 | Wach | G01N 21/474 356/301 |

(Continued)

FOREIGN PATENT DOCUMENTS

JP   5505578 B1   5/2014

OTHER PUBLICATIONS

Kong et al., "A novel non-imaging optics based Raman spectroscopy device for transdermal blood analyte measurement", AIP Advances 1, 2011, 13 pages total.

(Continued)

*Primary Examiner* — Tarifur R Chowdhury
*Assistant Examiner* — Omar H Nixon
(74) *Attorney, Agent, or Firm* — Sughrue Mion, PLLC

(57) ABSTRACT

A Raman probe includes: a light source configured to emit light onto an object; a light collector configured to collect Raman-scattered light from the object by reflecting the Raman-scattered light, the light collector including a light incident port, a light emitting port, and a reflective surface including a light incident port portion and a light emitting port portion, a slope of the light incident port portion with respect to an optical axis of the light collector being smaller than a slope of the light emitting port portion with respect to the optical axis; a condenser lens configured to collect the Raman-scattered light collected by the light collector; and a photodetector configured to detect the Raman-scattered light collected by the condenser lens.

28 Claims, 11 Drawing Sheets

(56) References Cited

U.S. PATENT DOCUMENTS

| | | | |
|---|---|---|---|
| 6,373,567 B1* | 4/2002 | Wise | G01J 3/1838 |
| | | | 356/301 |
| 6,795,177 B2 | 9/2004 | Doyle | |
| 8,107,069 B2 | 1/2012 | Wang et al. | |
| 8,369,669 B2 | 2/2013 | Bouma et al. | |
| 9,523,804 B2 | 12/2016 | Wach | |
| 9,606,063 B2 | 3/2017 | Lee et al. | |
| 9,662,047 B2 | 5/2017 | Barman et al. | |
| 9,958,615 B2 | 5/2018 | Tedesco | |
| 2003/0081206 A1* | 5/2003 | Doyle | G01J 3/44 |
| | | | 356/301 |
| 2006/0023837 A1* | 2/2006 | He | G01N 23/227 |
| | | | 378/70 |
| 2015/0216417 A1 | 8/2015 | Huang et al. | |
| 2015/0377787 A1* | 12/2015 | Zeng | A61B 5/0075 |
| | | | 356/301 |
| 2016/0177366 A1 | 6/2016 | Auner et al. | |
| 2018/0136133 A1* | 5/2018 | Zhao | G01N 21/65 |

OTHER PUBLICATIONS

Tian et al., "Efficiency enhancement of Raman spectroscopy at long working distance by parabolic reflector", Biomedical Optics Express, vol. 8, No. 11, 2017, 10 pages total.

Coster et al. "Free-Form Optics Enhanced Confocal Raman Spectroscopy for Optofluidic Lab-on-Chips", IEEE Journal of Selected Topics in Quantum Electronics, vol. 21, No. 4, 2015, 8 pages total.

* cited by examiner

RAMAN PROBE AND BIOLOGICAL COMPONENT ANALYZING APPARATUS USING THE SAME

CROSS-REFERENCE TO RELATED APPLICATION(S)

This application claims priority from Korean Patent Application No. 10-2018-0089268, filed on Jul. 31, 2018, in the Korean Intellectual Property Office, the entire disclosure of which is incorporated herein by reference for all purposes.

BACKGROUND

1. Field

Example embodiments of the present disclosure relate to a Raman probe and a biological component analyzing apparatus using the same.

2. Description of Related Art

Non-invasive biological sensors, using spectroscopic analysis techniques such as Raman spectroscopy, may improve user convenience as the sensors may measure blood components without drawing blood. Particularly, such non-invasive analysis techniques may be used to predict a signal of a blood component by analyzing interstitial fluid present in a dermal layer based on each individual's measured skin spectrum. However, the non-invasive biological sensors have drawbacks in that a measured amount of Raman signal is generally small, and when the Raman signal is measured from turbid media, such as skin, using an existing image-based examination optical system and a Raman probe in the form of an endoscope, Raman light collection efficiency is very low.

SUMMARY

Example embodiments provide a Raman probe and a biological component analyzing apparatus using the same, in which light collection efficiency may be increased.

In accordance with an aspect of an example embodiment, a Raman probe includes a light source configured to emit light onto an object; a light collector configured to collect Raman-scattered light from the object by reflecting the Raman-scattered light, the light collector including a light incident port; a light emitting port; and a reflective surface including a light incident port portion and a light emitting port portion, a slope of the light incident port portion with respect to an optical axis of the light collector being smaller than a slope of the light emitting port portion with respect to the optical axis; a condenser lens configured to collect the Raman-scattered light collected by the light collector; and a photodetector configured to detect the Raman-scattered light collected by the condenser lens.

The light collector may include a body of revolution having the optical axis as a rotation axis.

The reflective surface may be provided on an inner circumferential surface of the light collector.

The slope of the reflective surface may increase from the light incident port toward the light emitting port.

A difference between an inner diameter of the light emitting port of the light collector and a clear aperture of the condensing lens may be equal to or smaller than a threshold value.

An optical axis direction length of the light collector may be equal to or smaller than 10 times the inner diameter of the light incident port.

A distance between the light collector and the condensing lens may be shorter than an optical axis direction length of the light collector.

The light collector may be further configured to reflect first Raman-scattered light from among the Raman-scattered light from the object incident upon the light collector at an angle greater than an acceptance angle of the condensing lens, and may be further configured not to reflect second Raman-scattered light from among the Raman-scattered light from the object incident upon the light collector at an angle equal to or smaller than the acceptance angle of the condensing lens.

An inner diameter of the light collector may be determined based on an inner radius of the light incident port, the slope of the light incident port portion, and an optical axis direction length of the light collector.

The inner radius of the light incident port and the slope of the light incident port portion may be determined based on at least one from among a Numerical Aperture of the condenser lens, a size of the photodetector, and a maximum divergence angle capable of being detected by the photodetector.

The Raman probe may further include an optical fiber interposed between the condensing lens and the photodetector.

In accordance with an aspect of another example embodiment, a Raman probe includes a light source configured to emit light onto an object; a light collector configured to collect Raman-scattered light from the object by reflecting the Raman-scattered light, the light collector including a light incident port; a light emitting port; and a reflective surface including a light incident port portion and a light emitting port portion, a slope of the light incident port portion with respect to an optical axis of the light collector being smaller than a slope of the light emitting port portion with respect to the optical axis; and a photodetector configured to detect the Raman-scattered light collected by the light collector.

The light collector may include a body of revolution having the optical axis as a rotation axis.

The reflective surface may be provided on an inner circumferential surface of the light collector.

The slope of the reflective surface may increase from the light incident port toward the light emitting port.

An optical axis direction length of the light collector may be equal to or smaller than 10 times the inner diameter of the light incident port.

A distance between the light collector and the photodetector may be shorter than an optical axis direction length of the light collector.

The light collector may be further configured to reflect first Raman-scattered light from among the Raman-scattered light from the object incident upon the light collector at an angle greater than a maximum divergence angle capable of being detected by the photodetector, and may be further configured not to reflect second Raman-scattered light from among the Raman-scattered light from the object incident upon the light collector at an angle equal to or smaller than the maximum divergence angle capable of being detected by the photodetector.

An inner diameter of the light collector may be determined based on an inner radius of the light incident port, the slope of the light incident port portion, and an optical axis direction length of the light collector.

The inner radius of the light incident port and the slope of the light incident port portion may be determined based on at least one from among a size of the photodetector and a maximum divergence angle capable of being detected by the photodetector.

In accordance with an aspect of another example embodiment, a Raman probe includes a light reflector, wherein an interior surface of the light reflector is configured to reflect light Raman-scattered by an object; and a photodetector configured to detect the light Raman-scattered by the object and light reflected by the interior surface of the light reflector.

The light reflector nay include a body of revolution having an optical axis of the light reflector as a rotation axis.

A diameter of a circular light inlet port of the light reflector may be less than a diameter of a circular light outlet port of the light reflector.

A diameter of the light reflector may gradually increase from a circular light inlet port of the light reflector to a circular light outlet port of the light reflector.

An optical axis direction length of the light reflector may be less than or equal to 10 times a diameter of a circular light inlet port of the light reflector.

A distance between the light reflector and the photodetector may be less than an optical axis direction length of the light reflector.

A first portion of the light Raman-scattered by the object may pass through an inlet port of the light reflector and may be reflected by the interior surface of the light reflector, and a second portion of the light Raman-scattered by the object may pass through the inlet port of the light reflector and may not be reflected by the interior surface of the light reflector.

A first scattering angle of the first portion of the light Raman-scattered by the object may be greater than a predetermined scattering angle, and a second scattering angle of the second portion of the light Raman-scattered by the object may be less than or equal to the predetermined scattering angle.

BRIEF DESCRIPTION OF THE DRAWINGS

The above and/or other aspects will become apparent and more readily appreciated from the following description of example embodiments, taken in conjunction with the accompanying drawing, in which.

DETAILED DESCRIPTION

Figure 1:
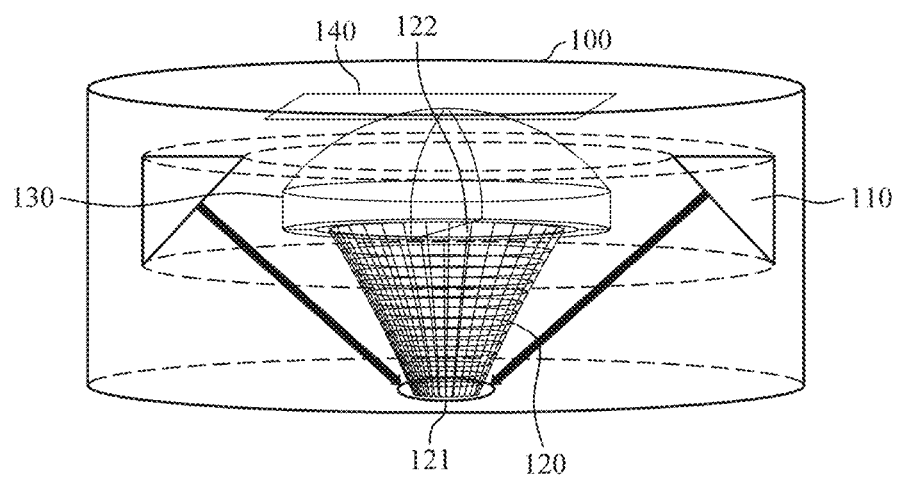
FIG. 1 is a diagram illustrating a Raman probe according to an example embodiment.

Hereinafter, example embodiments of the present disclosure will be described in detail with reference to the accompanying drawings. In the drawings, the same reference symbols refer to same parts although illustrated in other drawings. In the following description, a detailed description of known functions and configurations incorporated herein will be omitted when it may obscure the subject matter of the present disclosure.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to example embodiments, and can be varied according to a purpose of a user or manager, or precedent and so on. Therefore, definitions of the terms should be made on the basis of the overall context.

Although the terms first, second, etc. may be used herein to describe various elements, these elements should not be limited by these terms. These terms are merely used to distinguish one element from another. Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Further, components that will be described in the specification are discriminated merely according to functions mainly performed by the components. That is, two or more components may be integrated into a single component. Furthermore, a single component may be separated into two or more components. Moreover, each component may additionally perform some or all of a function executed by another component in addition to the main function thereof. Some or all of the main function of each component may be carried out by another component. Each component may be implemented as hardware, software, or a combination of both.

Throughout the drawings and the detailed description, unless otherwise described, the same drawing reference numerals will be understood to refer to the same elements, features, and structures. The relative size and depiction of these elements may be exaggerated for clarity, illustration, and convenience.

Figure 2:
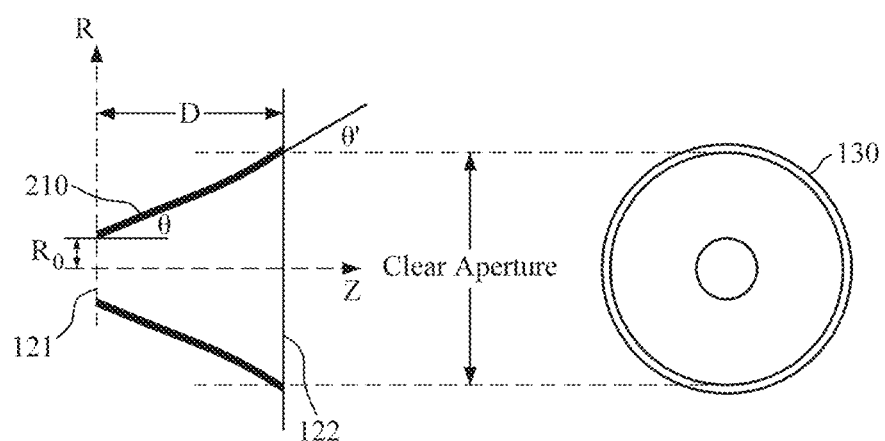
FIG. 2 is a diagram explaining a reflective surface of a light collector according to an example embodiment.

FIG. 1 is a diagram illustrating an example of a Raman probe according to an example embodiment; and FIG. 2 is a diagram explaining a reflective surface of a light collector according to an example embodiment.

Referring to FIGS. 1 and 2, the Raman probe 100 includes a light source unit 110, a light collector 120 (i.e., light reflector), a condenser lens 130, and a photodetector 140.

The light source unit 110 may emit light onto a sample. To this end, the light source unit 110 may include one or more light sources. For example, the light source may emit light of a predetermined wavelength, e.g., visible light or infrared light, onto a sample. However, the light source is not limited thereto, and wavelengths of light emitted by the light source may vary depending on the purpose of measurement, an object to be analyzed, and the like. Further, the light source is not necessarily a single light emitting body, but may be an array of a plurality of light emitting bodies. In the case where the light source is configured as an array of a plurality of light emitting bodies, the plurality of light emitting bodies may each emit light of a wavelength different from that of light emitted by other light emitting bodies according to the purpose of measurement, or all the light emitting bodies may emit light of the same wavelength. In an example embodiment, the light source may be a light emitting diode (LED), a laser diode, and the like. However, this is merely an example, and the light source is not limited thereto.

In an example embodiment, the light source unit 110 may further include a filter (e.g., long pass filter, clean-up filter, band-pass filter, etc.) for selecting light of a specific wavelength, and/or an optical element (e.g., reflection mirror, etc.) for directing the emitted light toward a desired position on the skin of an object.

In an example embodiment, the light source unit 110 may be disposed on the left, right, front, and rear sides of the light collector 120 or a condenser lens 130, so as to emit light obliquely from the side of the light collector 120 or the condenser lens 130 onto an object positioned beneath the light collector 120 or the condenser lens 130.

The light collector 120 may primarily collect light by reflecting Raman-scattered light from the object. The light collector 120 includes an inner circumferential surface and an outer circumferential surface, and is a body of revolution having an optical axis (z axis) as a rotation axis, and a reflective surface formed on the inner circumferential surface. In other words, a shape of the light collector 120 may be determined by rotating a planar shape that is coplanar with the optical axis around the optical axis.

The light collector 120 includes a light incident port 121 (i.e., circular light inlet port), through which Raman-scattered light from the object is incident, and a light emitting port 122 (i.e., circular light outlet port) through which the incident Raman-scattered light is emitted. The Raman-scattered light may pass through the light incident port 121 and the light emitting port 122.

The inner circumferential surface of the light collector 120 may be plated with metal (e.g., gold) having high light reflectivity, so as to reflect all or a portion of the Raman-scattered light incident through the light incident port 121. However, the inner circumferential surface of the light collector 120 is not limited thereto, and may be formed as a reflector and the like.

With respect to the optical axis (z axis)), a reflective surface of the light incident port 121 of the light collector 120 may be formed to have a smaller slope tan θ than a slope tan θ' of a reflective surface of the light emitting port 122. In this case, the slope of the reflective surface may indicate a slope of a tangent line in an optical axis direction of a reflective surface based on the optical axis (z axis). In other words, the angle θ between the optical axis and the reflective surface at the light incident port 121 may be smaller than the angle θ between the optical axis and the reflective surface at the light emitting port 122. In an example embodiment, the slope of the reflective surface of the light collector may become larger from the light incident port 121 toward the light emitting port 122.

The light collector 120 may reflect only the Raman-scattered light is incident upon the light collector 120 at an angle greater than a specific angle, among the incident Raman-scattered light rays. For example, the light collector 120 may reflect Raman-scattered light incident at an angle exceeding an acceptance angle of the condenser lens 130, among the incident Raman-scattered light rays, and may not reflect Raman-scattered light of the condenser lens 130 which is incident at an angle equal to or smaller than the acceptance angle of the condenser lens 130, among the incident Raman-scattered light rays.

An inner radius r for each optical axis direction position of the light collector 120 may be determined based on an inner radius $R_0$ of the light incident port 121, a slope tan θ of the reflective surface of the light incident port 121, and an optical axis direction position z. For example, the inner radius for each optical axis direction position of the light collector 120 may be determined by Equation 1.

$$r^2 = R_0[+1+2z \tan θ + a_2 z^2 + a_3 z^3 + a_4 z^4 + a_5 z^5] \qquad [\text{Equation 1}]$$

Herein, $a_2$, $a_3$, $a_4$, and $a_5$ may denote coefficients, in which the inner radius $R_0$ of the light incident port 121, the slope tan θ of the reflective surface of the light incident port 121, and the coefficients, $a_2$, $a_3$, $a_4$, and $a_5$ be determined by considering system characteristics and specifications such as a Numerical Aperture (NA) of the condenser lens 130, the size of the photodetector 140, a maximum divergence angle capable of being detected by the photodetector 140, and the like.

The inner circumferential surface, i.e., a reflective surface, of the light collector 120 may be formed by rotating a curve 210 about the optical axis (z a as a rotation axis.

The inner diameter of the light emitting port 122 of the light collector 120 may be the same as or similar to a clear aperture of the condenser lens 130, so that all the light rays, having passed through the light collector 120, may pass through the clear aperture f the condenser lens 130. For example, a difference between the inner diameter of light emitting port 122 of the light collector 120 and the clear aperture of the condenser lens 130 may be equal to or smaller than a predetermined threshold value. Further, the optical axis direction length D of the light collector 120 may be equal to or smaller than 10 times the diameter of the inner diameter $2R_0$ of the light incident port 121.

The condenser lens 130 may secondarily collect the Raman-scattered light which has been primarily collected by the light collector 120.

A distance between the light collector 120 and the condenser lens 130 may be shorter than the optical axis direction length of the light collector 120. That is, the light collector 120 and the condenser lens 130 may be disposed so that the distance between the light collector 120 and the condenser lens 130 may be shorter than the optical axis direction length of the light collector 120.

The photodetector 140 may detect the Raman-scattered light which has been secondarily collected by the condenser lens 130. In an example embodiment, the photodetector 140 may include a photo diode, a photo transistor, a Complementary metal-oxide-semiconductor (CMOS), a charge-coupled device (CCD), and the like. The photodetector 140 is not necessarily a single device, and may be an array of a plurality of devices.

While FIG. 1 illustrates one light collector, the light collector is not limited thereto. That is, according to a shape of the photodetector 140 and an object, the photodetector 140 may include an array of a plurality of light collectors.

Figure 3:
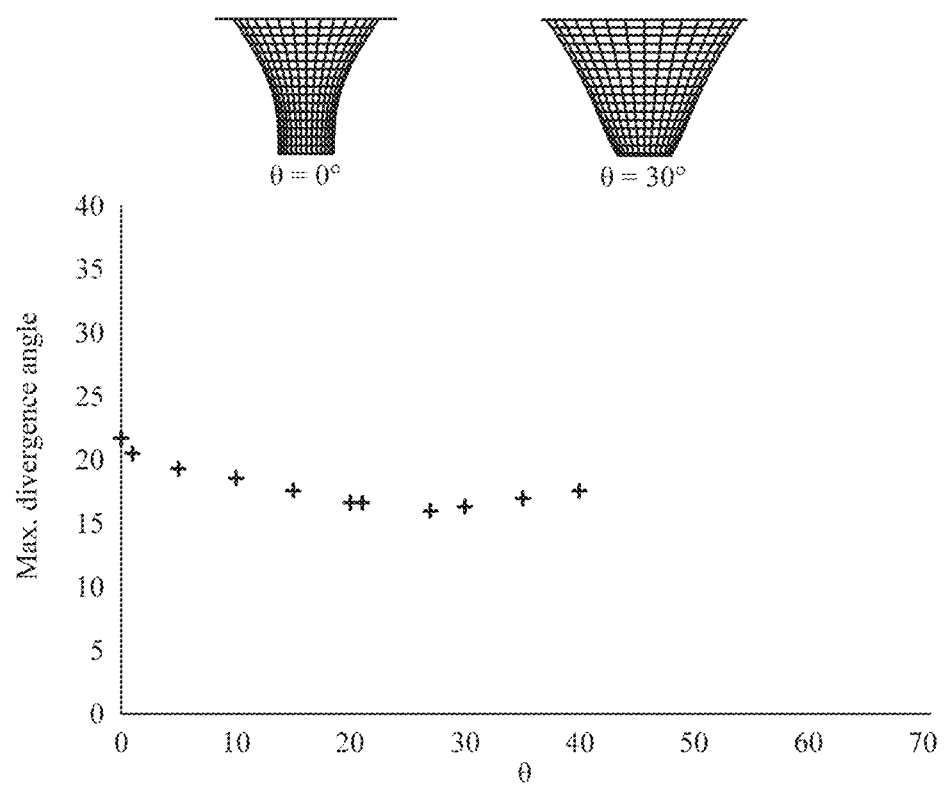
FIG. 3 is a diagram illustrating an example of a maximum divergence angle of light reaching a photodetector according to a slope of a reflective surface of a light incident port of a light collector.

FIG. 3 is a diagram illustrating an example of a maximum divergence angle of light reaching a photodetector according to a slope of a reflective surface of a light incident port of a light collector. More specifically, FIG. 3 illustrates a maximum divergence angle of the collected light according to a slope of a reflective surface of a light incident port in the case where an inner radius $R_0$ of the light incident port is $R_0=1$ mm, NA of a condenser lens is NA=0.5, $a_2=a_4=a_5=0$, and $a_3=0.5$, i.e., in the case where Equation 1 is $r^2=1+2z \tan \theta+0.05z^3$.

Referring to FIG. 3, in the case where a slope angle $\theta$ of the reflective surface of the light incident port is around 30°, the maximum divergence angle of light reaching the photodetector is minimized. This may indicate that in the case where the slope angle $\theta$ of the reflective surface of the light incident port is similar to an acceptance angle of the condenser lens (in the illustrated example, NA of the condenser lens is NA=0.5, such that the acceptance angle of the condenser lens is 30°), the maximum divergence angle of light reaching the photodetector is minimized.

Figure 4:
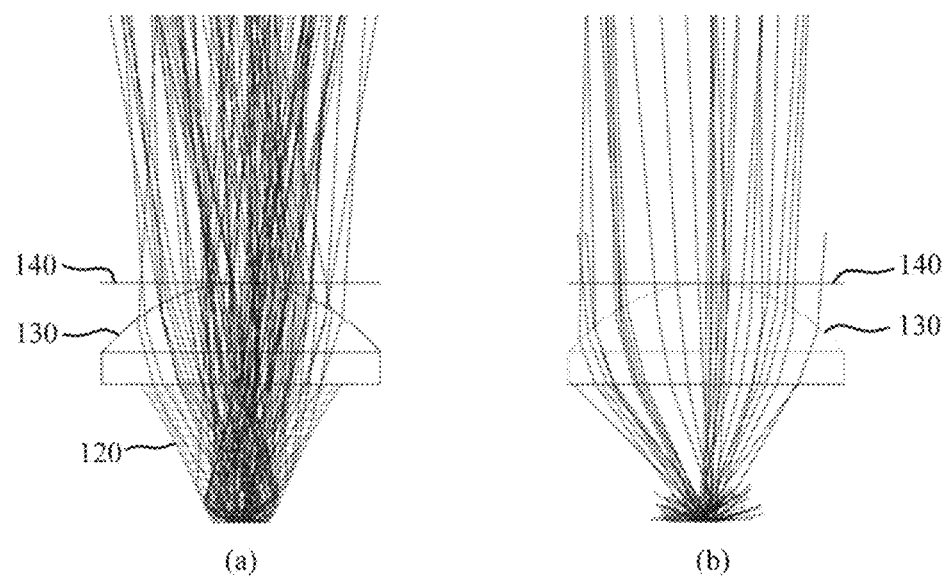
FIG. 4 is a diagram illustrating an example of comparing a degree of light collection between a case of using a light collector and a condenser lens and a case of using only the condenser lens.

FIG. 4 is a diagram illustrating an example of comparing a degree of light collection between a case of using a light collector and a condenser lens and a case of using only the condenser lens.

Referring to FIG. 4, in the case of (a) using the light collector 120 and the condenser lens 130, Raman-scattered light (e.g., Raman-scattered light emitted from the surface of an object), incident at an angle greater than an acceptance angle of the condenser lens 130, is reflected from the reflective surface of the light collector 120, such that divergence angle is changed to an angle equal to or miler than the acceptance angle of the condenser lens 130. Accordingly, Raman-scattered light incident upon the light collector 120 at an angle greater than the acceptance angle of the condenser lens 130 may also be collected to be transferred to the condenser lens 130.

By contrast, in the case of (b) using only the condenser lens 130 without the light collector 120, Raman-scattered light incident upon the condenser lens 130 at an angle greater than the acceptance angle of the condenser lens 130 may not be transferred to the condenser lens 130.

That is, it can be seen that in the case of (a) using the light collector 120 and the condenser lens 130, light collection efficiency may be greatly improved compared to the case of (b) using only the condenser lens 130 without the light collector 120.

Figure 5:
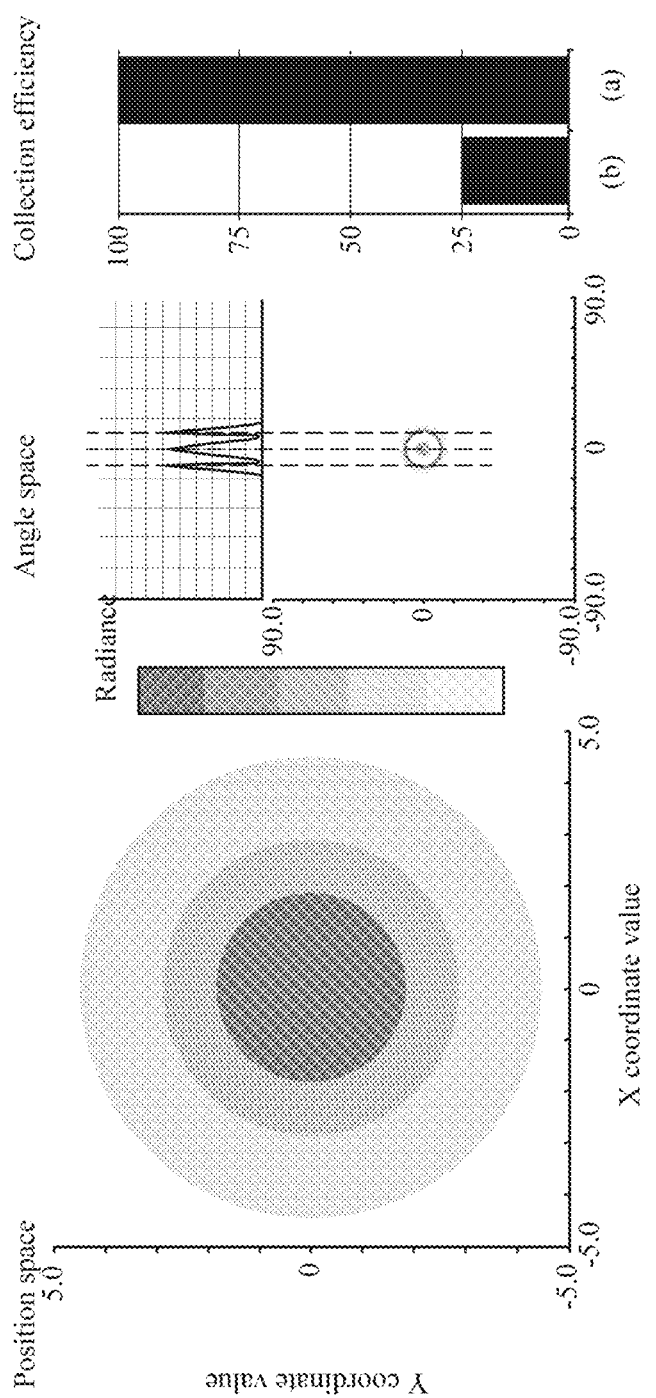
FIG. 5 is a diagram illustrating a simulation result of light collection efficiency of a Raman probe according to an example embodiment.

FIG. 5 is a diagram illustrating a simulation result of light collection efficiency of a Raman probe according to an example embodiment. More FIG. 5 illustrates a simulation result of a Raman probe in the case where an inner radius $R_0$ of an incident opening is $R_0=1$ mm, a slope angle of a reflective surface of the light incident port 121 is $\theta=30°$, NA of a condenser lens is NA=0.5, $a_2=a_4=a_5=0$, and $a_3=0.5$, in the case where Equation 1 is $r^2=1+2z \tan \theta+0.05z^3$.

As illustrated in FIG. 5, it can be seen that in an ideal case where Raman-scattered light is emitted in a uniform hemispherical pattern at a solid angle of $2\pi$ on a surface of a sample having a diameter of 1 mm (light reflectance of a reflective surface=100%), a simulation result shows light collection efficiency of 99% or higher (in the illustrated example, 49,999,927 of 50,000,000 light rays are detected) when (a) using the light collector and the condenser lens; by contrast, a simulation result shows light collection efficiency of about 25% when (b) using only the condenser lens.

As further illustrated in FIG. 5, in the case of (a) using the light collector and the condenser lens, light is detected in a space having a diameter of 10 mm as shown in a position space graph, and a divergence angle of the detected light is equal to or smaller than 16° as shown in an angle space graph.

Figure 6:
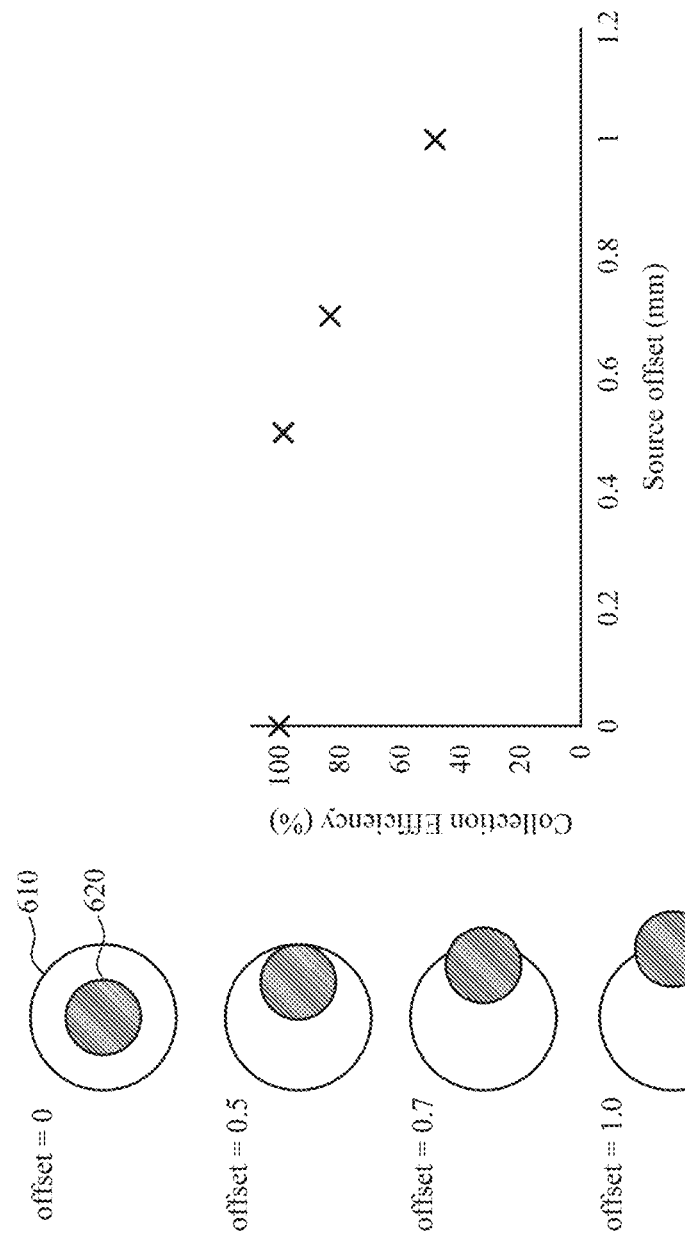
FIG. 6 is a diagram illustrating an example of light collection efficiency of a Raman probe in the case where there is a Raman source offset.

FIG. 6 is a diagram illustrating an example of light collection efficiency of a Raman probe in the case where there is a Raman source offset. FIG. 6 illustrates light collection efficiency for each Raman source offset of a Raman probe in the case where an inner radius $R_0$ of a light incident port $R_0=1$ mm, a slope angle of a reflective surface of the light incident port is $\theta=30°$, NA of a condenser lens is NA=0.5, $a_2=a_4=a_5=0$, and $a_3=0.5$, i.e., in the case where Equation 1 is $r^2=1+2z \tan \theta+0.05z^3$. Here, the Raman source may indicate a sample area onto which light is emitted and from which light is Raman-scattered. In the illustrated example, it is assumed that the Raman source has a diameter of 1 mm.

Referring to FIG. 6, in the case where the Raman source 620 is within a light incident port area 610 (in the case where an offset is 0 mm and 0.5 mm), light collection efficiency is almost 100%. By contrast, in the case where the Raman source 620 deviates from the light incident port area 610 (in the case where an offset is 0.7 mm), light collection efficiency is sharply decreased.

That is, even when there is an offset of the Raman source 620 in an x axis direction or a y axis direction, light collection efficiency of the Raman probe according to an example embodiment of the present disclosure may be maintained at a high level if the Raman source 620 does not deviate from the light incident port 610 of the light collector.

Figure 7:
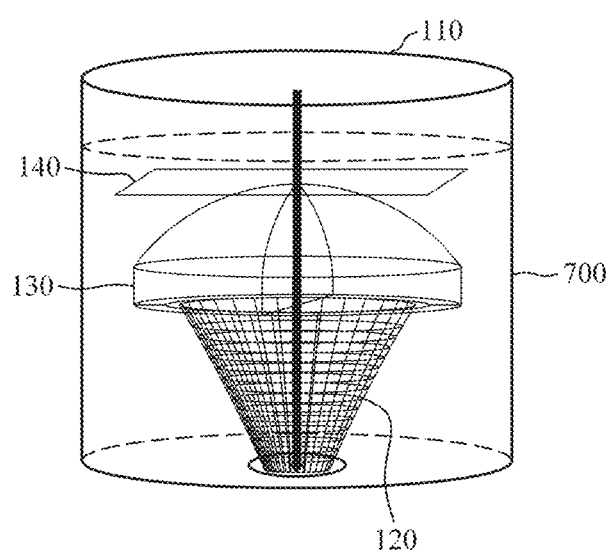
FIG. 7 is a diagram illustrating a Raman probe according to an example embodiment.

FIG. 7 is a diagram illustrating a Raman probe according to an example embodiment.

Referring to FIG. 7, the Raman probe 700 includes a light source unit 110, a light collector 120, a condenser lens 130, and a photodetector 140.

When compared to the Raman probe 100 of FIG. 1, a position of the light source unit 110 of the Raman probe 700 of FIG. 7 is different. That is, in the Raman probe 700 of FIG. 7, the light source unit 110 is disposed above the photodetector 110 to emit light in a direction perpendicular to an optical axis.

In addition, the light source unit 110, the light collector 120, the condensing lens 130, and the photodetector 140 are described above in detail with reference to FIG. 1, such that detailed description thereof will be omitted here.

Figure 8:
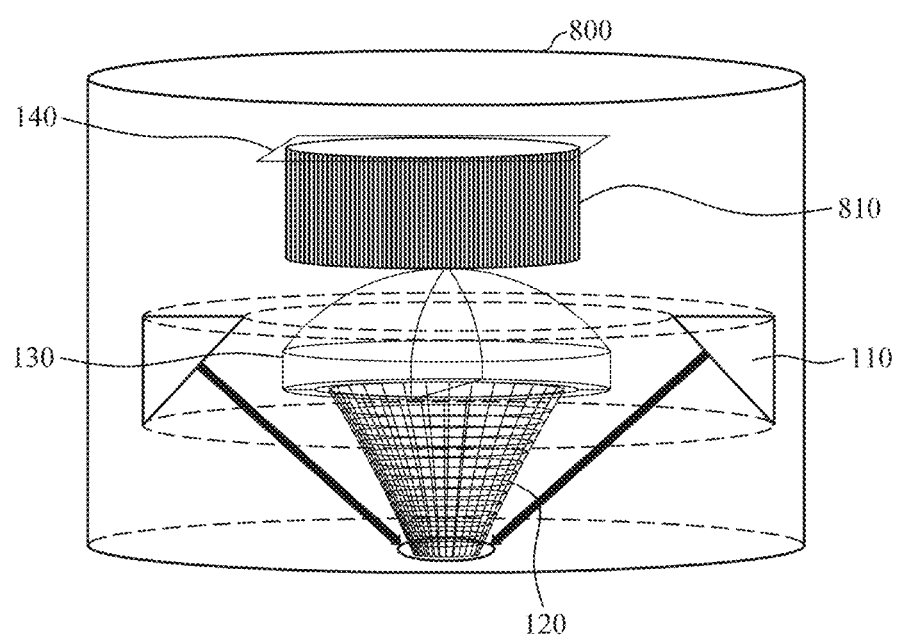
FIG. 8 is a diagram illustrating a Raman probe according to an example embodiment.

FIG. 8 is a diagram illustrating a Raman probe according to an example embodiment.

Referring to FIG. 8, the Raman probe 800 includes a light source unit 110, a light collector 120, a condensing lens 130, a photodetector 140, and an optical fiber 810.

When compared to the Raman probe 100 of FIG. 1, the Raman probe 800 of FIG. 8 may further include the optical fiber 810 which is interposed between the condensing lens 130 and the photodetector 140. That is, in the Raman probe 800 of FIG. 8, Raman-scattered light, which has been secondarily focused by the condenser lens 130, may pass through the optical fiber 810 to be detected by the photodetector 110.

In addition, the light source unit 110, the light collector 120, the condensing lens 130, and the photodetector 140 are described above in detail with reference to FIG. 1, such that detailed description thereof will be omitted here.

Figure 9:
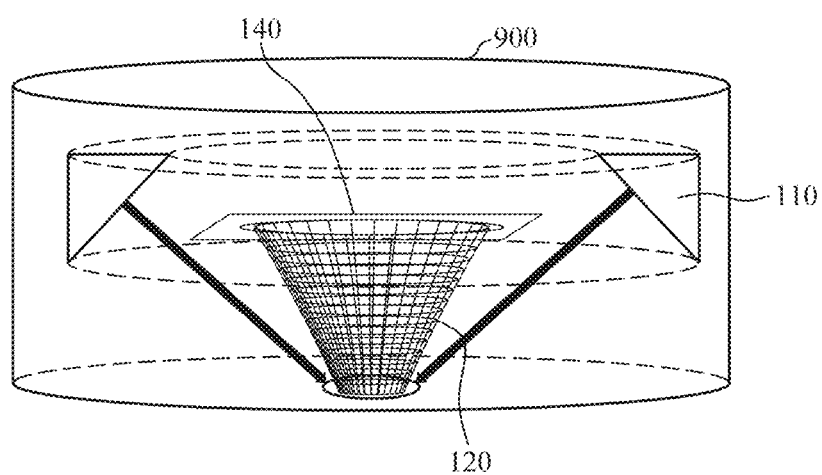
FIG. 9 is a diagram illustrating a Raman probe according to an example embodiment.

FIG. 9 is a diagram illustrating a Raman probe according to an example embodiment.

Referring to FIG. 9, the Raman probe 900 includes a light source unit 110, a light collector 120, and a photodetector 140.

When compared to the Raman probe 100 of FIG. 1, the Raman probe 900 of FIG. 9 may not include the condensing lens 130. That is, in the Raman probe 900 of FIG. 9, the photodetector 140 may detect light collected by the light collector 120.

In this case, the light collector 120 may reflect Raman-scattered light incident upon the light collector 120 at an angle greater than a maximum divergence angle which may be detected by the photodetector 140, among the Raman-scattered light rays from an object, and may not reflect Raman-scattered light incident upon the light collector 120 at an angle equal to or smaller than the maximum divergence angle which may be detected by the photodetector 140. Further, the distance between the light collector 120 and the photodetector 140 may be shorter than an optical axis direction length of the light collector 120.

In addition, the light source unit 110, the light collector 120, and the photodetector 140 are described above in detail with reference to FIG. 1, such that detailed description thereof will be omitted here.

Figure 10:
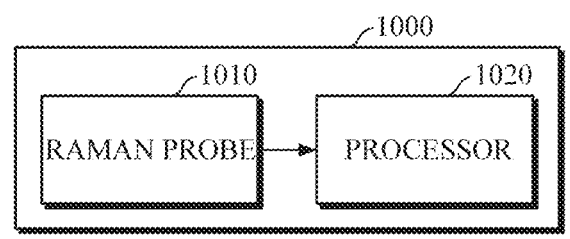
FIG. 10 is a block diagram illustrating an example of a biological component estimating apparatus according to an example embodiment.

FIG. 10 is a block diagram illustrating a biological component estimating apparatus according to an example embodiment.

Referring to FIG. 10, the biological component estimating apparatus 100 includes a Raman probe 1010 and a processor 1020. Here, the Raman probe 1010 may be any of the Raman probes 100, 700, 800, and 900 described above with reference to FIGS. 1 to 9, such that detailed description thereof will be omitted here.

The processor 1020 may control the overall operation of the biological component estimating apparatus 1000, and may process various signals related to the operation of the biological component estimating apparatus 1000.

The processor 1020 may obtain a Raman spectrum of an object based on Raman-scattered light detected by the Raman probe 1010.

In addition, the processor 1020 may estimate a value of a biological component of the object by analyzing the obtained Raman spectrum. Here, the biological component may include blood glucose, cholesterol, triglycerides, proteins, uric acid, and the like; and skin components such as collagen, keratin, elastin, and the like.

Figure 11:
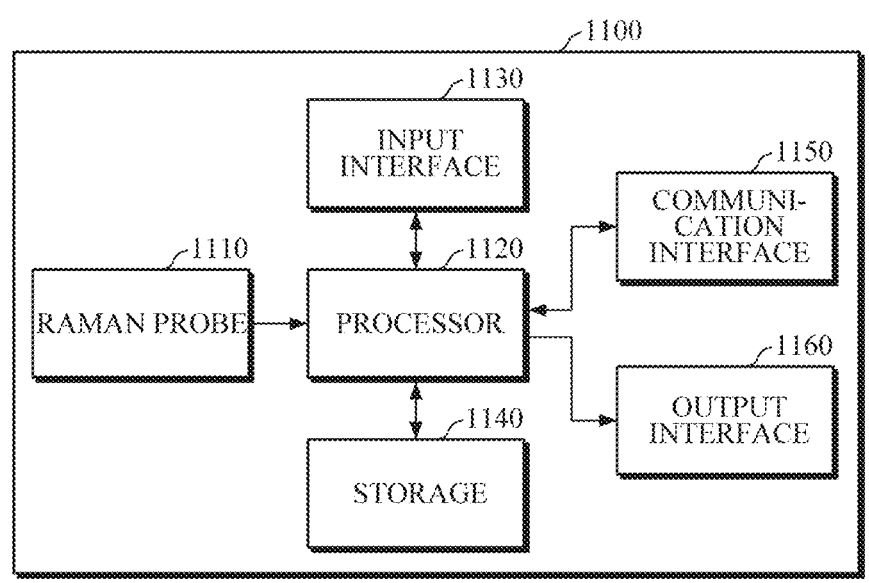
FIG. 11 is a block diagram illustrating a biological component analyzing apparatus according to an example embodiment.

FIG. 11 is a block diagram illustrating a biological component analyzing apparatus according to an example embodiment.

Referring to FIG. 11, the biological component analyzing apparatus 1100 includes a Raman probe 1110, a processor 1120, an input interface 1130, a storage 1140, a communication interface 1150, and an output interface 1160. Here, the Raman probe 1110 and the processor 1120 are the same as the Raman probe 1010 and the processor 1020 of FIG. 10, such that detailed description thereof will be omitted here.

The input interface 1130 may receive input of various operation signals from a user. In an example embodiment, the input interface 1130 may include a keypad, a dome switch, a touch pad (static pressure/capacitance), a jog wheel, a jog switch, a hardware (H/W) button, and the like. Particularly, the touch pad, which forms a layer structure with a display, may be a touch screen.

The storage 1140 may store programs or commands for operation of the biological component analyzing apparatus 1100 and may store data input to and output from the biological component analyzing apparatus 1100. Further, the storage 1140 may store the obtained Raman spectrum and/or the estimated bio-information of an object, and the like.

The storage 1140 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the biological component analyzing apparatus 1100 may operate an external storage medium, such as web storage and the like, which performs a storage function of the storage 1140 on the Internet.

The communication interface 1150 may perform communication with an external device. For example, the communication interface 1150 may transmit, to the external device, data input by a user, the Raman spectrum and/or the bio-information of an object, and the like; or may receive, from the external device, various data useful for obtaining a Raman spectrum and/or estimating bio-information.

In this case, the external device may be medical equipment using the data input by a user, the Raman spectrum and/or the bio-information of an object, and the like, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation device, an MP3 player, a digital camera, a wearable device, and the like, but is not limited thereto.

The communication interface 1150 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely an example and is not intended to be limiting.

The output interface 1160 may output the data input by a user, the Raman spectrum and/or the bio-information of an object, and the like. In an example embodiment, the output interface 1160 may output the data input by a user, the Raman spectrum and/or the bio-information of an object, and the like by using at least one from among an acoustic method, a visual method, and a tactile method. To this end, the output interface 1160 may include a display, a speaker, a vibrator, and/or the like.

Embodiments of the present disclosure can be realized as a computer-readable code stored in a non-transitory a computer-readable recording medium. Codes and code segments needed for realizing the present disclosure can be deduced by computer programmers of ordinary skill in the art. The non-transitory computer-readable recording medium may be any type of recording device in which data is stored in a computer-readable manner. Examples of the non-transitory computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

Example embodiments have been described herein. However, it will be obvious to those skilled in the art that various modifications can be made without departing from the gist of the present disclosure. Therefore, it is to be understood that that the scope of the present disclosure is not limited to the above-mentioned example embodiments, but is intended to include various modifications and equivalents included within the spirit and scope of the appended claims.

What is claimed is:

1. A Raman probe comprising:
   a light source configured to emit light onto an object;
   a light collector configured to collect Raman-scattered light from the object by reflecting the Raman-scattered light, the light collector comprising:
   a light incident port;
   a light emitting port; and
   a reflective surface comprising a light incident port portion at a first end at a surface of the object and a light emitting port portion at a second end opposite to the first end, a non-zero slope of the light incident port portion with respect to an optical axis of the light collector being smaller than a non-zero slope of the light emitting port portion with respect to the optical axis such that a slope of the reflective surface increases from the first end to the second end;
   a condensing lens configured to collect the Raman-scattered light collected by the light collector; and
   a photodetector configured to detect the Raman-scattered light collected by the condensing lens.

2. The Raman probe of claim 1, wherein the light collector is a body of revolution having the optical axis as a rotation axis.

3. The Raman probe of claim 1, wherein the reflective surface is provided on an inner circumferential surface of the light collector.

4. The Raman probe of claim 1, wherein the slope of the reflective surface increases from the light incident port toward the light emitting port.

5. The Raman probe of claim 1, wherein a difference between an inner diameter of the light emitting port of the light collector and a clear aperture of the condensing lens is equal to or smaller than a threshold value.

6. The Raman probe of claim 1, wherein an optical axis direction length of the light collector is equal to or smaller than 10 times an inner diameter of the light incident port.

7. The Raman probe of claim 1, wherein a distance between the light collector and the condensing lens is shorter than an optical axis direction length of the light collector.

8. The Raman probe of claim 1, wherein the light collector is further configured to reflect first Raman-scattered light from among the Raman-scattered light from the object incident upon the light collector at an angle greater than an acceptance angle of the condensing lens, and is further configured not to reflect second Raman-scattered light from among the Raman-scattered light from the object incident upon the light collector at an angle equal to or smaller than the acceptance angle of the condensing lens.

9. The Raman probe of claim 1, wherein an inner diameter of the light collector is determined based on an inner radius of the light incident port, the slope of the light incident port portion, and an optical axis direction length of the light collector.

10. The Raman probe of claim 9, wherein the inner radius of the light incident port and the slope of the light incident port portion are determined based on at least one from among a Numerical Aperture of the condensing lens, a size of the photodetector, and a maximum divergence angle capable of being detected by the photodetector.

11. The Raman probe of claim 1, further comprising an optical fiber interposed between the condensing lens and the photodetector.

12. A Raman probe comprising:
    a light source configured to emit light onto an object;
    a light collector configured to collect Raman-scattered light from the object by reflecting the Raman-scattered light, the light collector comprising:
    a light incident port;
    a light emitting port; and
    a reflective surface comprising a light incident port portion at a first end at a surface of the object and a light emitting port portion at a second end opposite to the first end, a non-zero slope of the light incident port portion with respect to an optical axis of the light collector being smaller than a non-zero slope of the light emitting port portion with respect to the optical axis such that a slope of the reflective surface increases from the first end to the second end; and
    a photodetector configured to detect the Raman-scattered light collected by the light collector.

13. The Raman probe of claim 12, wherein the light collector is a body of revolution having the optical axis as a rotation axis.

14. The Raman probe of claim 12, wherein the reflective surface is provided on an inner circumferential surface of the light collector.

15. The Raman probe of claim 12, wherein the slope of the reflective surface increases from the light incident port toward the light emitting port.

16. The Raman probe of claim 12, wherein an optical axis direction length of the light collector is equal to or smaller than 10 times an inner diameter of the light incident port.

17. The Raman probe of claim 12, wherein a distance between the light collector and the photodetector is shorter than an optical axis direction length of the light collector.

18. The Raman probe of claim 12, wherein the light collector is further configured to reflect first Raman-scattered light from among the Raman-scattered light from the object incident upon the light collector at an angle greater than a maximum divergence angle capable of being detected by the photodetector, and is further configured not to reflect second Raman-scattered light from among the Raman-scattered light from the object incident upon the light collector at an angle equal to or smaller than the maximum divergence angle capable of being detected by the photodetector.

19. The Raman probe of claim 12, wherein an inner diameter of the light collector is determined based on an inner radius of the light incident port, the slope of the light incident port portion, and an optical axis direction length of the light collector.

20. The Raman probe of claim 19, wherein the inner radius of the light incident port and the slope of the light incident port portion are determined based on at least one from among a size of the photodetector and a maximum divergence angle capable of being detected by the photodetector.

21. A Raman probe comprising:
    a light reflector comprising an interior surface configured to reflect light Raman-scattered by an object; and
    a photodetector configured to detect the light Raman-scattered by the object and light reflected by the interior surface of the light reflector, wherein the interior surface of the light reflector comprises a light incident port portion at a first end at a surface of the object and a light emitting port portion at a second end opposite to the first end, a non-zero slope of the light incident port portion with respect to an optical axis of the light reflector being smaller than a non-zero slope of the light emitting port portion with respect to the optical axis such that a slope of the interior surface increases from the first end to the second end.

22. The Raman probe of claim 21, wherein the light reflector is a body of revolution having the optical axis of the light reflector as a rotation axis.

23. The Raman probe of claim 22, wherein the light reflector further comprises a circular light inlet port and a circular light outlet port, and a diameter of the circular light inlet port of the light reflector is less than a diameter of the circular light outlet port of the light reflector.

24. The Raman probe of claim 21, wherein the light reflector further comprises a circular light inlet port and a circular light outlet port, and a diameter of the light reflector gradually increases from the circular light inlet port of the light reflector to the circular light outlet port of the light reflector.

25. The Raman probe of claim 23, wherein an optical axis direction length of the light reflector is less than or equal to 10 times the diameter of the circular light inlet port of the light reflector.

26. The Raman probe of claim 22, wherein a distance between the light reflector and the photodetector is less than an optical axis direction length of the light reflector.

27. The Raman probe of claim 21, wherein a first portion of the light Raman-scattered by the object passes through an inlet port of the light reflector and is reflected by the interior surface of the light reflector, and wherein a second portion of the light Raman-scattered by the object passes through the inlet port of the light reflector and is not reflected by the interior surface of the light reflector.

28. The Raman probe of claim 27, wherein a first scattering angle of the first portion of the light Raman-scattered by the object is greater than a predetermined scattering angle, and wherein a second scattering angle of the second portion of the light Raman-scattered by the object is less than or equal to the predetermined scattering angle.

* * * * *